United States Patent
Ahn et al.

(10) Patent No.: US 10,535,015 B2
(45) Date of Patent: Jan. 14, 2020

(54) WALKING ASSISTANCE APPARATUS AND METHOD OF CONTROLLING SAME

(71) Applicant: Samsung Electronics Co., Ltd., Suwon-si, Gyeonggi-do (KR)

(72) Inventors: Sunghwan Ahn, Seoul (KR); Youngbo Shim, Seoul (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 925 days.

(21) Appl. No.: 15/054,763

(22) Filed: Feb. 26, 2016

(65) Prior Publication Data

US 2017/0132527 A1     May 11, 2017

(30) Foreign Application Priority Data

Nov. 5, 2015   (KR) .......................... 10-2015-0154910

(51) Int. Cl.
| | | |
|---|---|---|
| *G06F 15/18* | (2006.01) | |
| *G06N 20/00* | (2019.01) | |
| *G16H 50/50* | (2018.01) | |
| *G16H 50/20* | (2018.01) | |
| *G06F 17/50* | (2006.01) | |
| *G06N 3/08* | (2006.01) | |
| *G06N 7/00* | (2006.01) | |

(52) U.S. Cl.
CPC ......... *G06N 20/00* (2019.01); *G06F 17/5009* (2013.01); *G06N 3/08* (2013.01); *G06N 7/005* (2013.01); *G16H 50/20* (2018.01); *G16H 50/50* (2018.01)

(58) Field of Classification Search
CPC ................................. G06F 1/163; G06N 3/004
USPC ....................................................... 706/15, 45
See application file for complete search history.

(56) References Cited

U.S. PATENT DOCUMENTS

| | | | |
|---|---|---|---|
| 2006/0284979 A1* | 12/2006 | Clarkson ................ | A61B 5/061 348/143 |
| 2008/0221487 A1 | 9/2008 | Zohar et al. | |
| 2010/0156653 A1 | 6/2010 | Chaudhari et al. | |
| 2011/0264015 A1 | 10/2011 | Endo | |
| 2012/0119904 A1* | 5/2012 | Coleman Boone .... | A61B 5/112 340/539.12 |

(Continued)

FOREIGN PATENT DOCUMENTS

| | | |
|---|---|---|
| EP | 2796123 A1 | 10/2014 |
| EP | 2899694 A2 | 7/2015 |

(Continued)

OTHER PUBLICATIONS

Extended European Search Report issued by the European Patent Office dated Mar. 20, 2017 for corresponding EP Patent Application No. 16190878.5.

(Continued)

*Primary Examiner* — David R Vincent
(74) *Attorney, Agent, or Firm* — Harness, Dickey and Pierce, P.L.C.

(57) ABSTRACT

A method and apparatus for training an algorithm to recognize a walking state of a user wearing a walking assistance apparatus are provided. The method and apparatus may generate virtual sensing data associated with walking of a virtual human model through a dynamic simulation, and may train the algorithm based on the virtual sensing data.

34 Claims, 11 Drawing Sheets

(56) References Cited

U.S. PATENT DOCUMENTS

| | | | |
|---|---|---|---|
| 2013/0226048 A1* | 8/2013 | Unluhisarcikli | A61H 3/00 601/34 |
| 2013/0310979 A1* | 11/2013 | Herr | B62D 57/032 700/258 |
| 2014/0226855 A1* | 8/2014 | Savvides | G06K 9/00771 382/103 |
| 2014/0277739 A1 | 9/2014 | Kornbluh et al. | |
| 2015/0045703 A1* | 2/2015 | Strausser | A61H 3/00 601/35 |
| 2015/0106052 A1* | 4/2015 | Balakrishnan | A61B 5/1123 702/150 |
| 2015/0157274 A1 | 6/2015 | Ghassemzadeh et al. | |
| 2015/0161511 A1 | 6/2015 | Ghassemzadeh et al. | |
| 2015/0269744 A1* | 9/2015 | Mukherjee | G06K 9/44 382/103 |
| 2016/0107309 A1* | 4/2016 | Walsh | B25J 9/0006 248/550 |
| 2017/0055880 A1* | 3/2017 | Agrawal | A61B 5/1038 |
| 2017/0090554 A1* | 3/2017 | Pececnik | G06F 3/011 |
| 2017/0243058 A1* | 8/2017 | Tan | G06K 9/00348 |

FOREIGN PATENT DOCUMENTS

| | | |
|---|---|---|
| JP | 1996221599 A | 8/1996 |
| JP | 1999085209 A | 3/1999 |
| JP | 2004163990 A | 6/2004 |
| KR | 1020110062044 A | 6/2011 |

OTHER PUBLICATIONS

Wright, Joe et al., "Intelligent Approaches in Locomotion—A Review", J. Intell Robot Syst (2015) 80:255-277.

Zhao, Cao-Yuan et al., "The Application of Machine-Learning on Lower Limb Motion Analysis in Human Exoskeleton System", S.S. Ge et al. (Eds.): ICSR 2012, LNAI 7621, pp. 600-611, 2012.

Ming Zeng et al., Convolutional Neural Networks for Human Activity Recognition Using Mobile Sensors, Mobile Computing, Application and Services (MobiCASE), Nov. 6-7, 2014, pp. 1-18.

Munif Alotaibi et al., "Automatic Real Time Gait Recognition based on Spatiotemporal Templates", Systems, Applications and Technology Conference (LISAT), 2015 IEEE, Long Island, pp. 1-5.

* cited by examiner

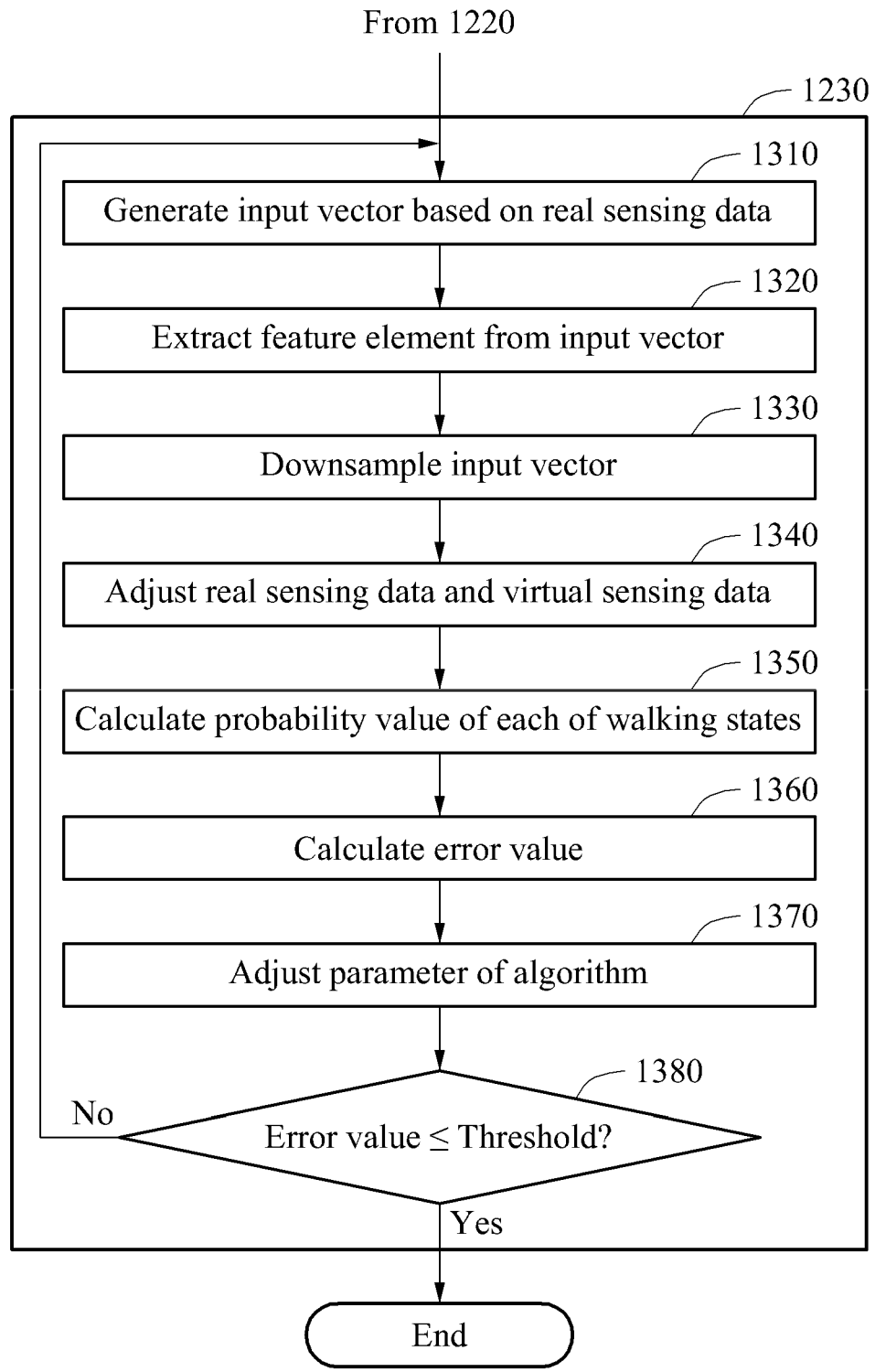

WALKING ASSISTANCE APPARATUS AND METHOD OF CONTROLLING SAME

CROSS-REFERENCE TO RELATED APPLICATION

This application claims under 35 U.S.C. § 119 to Korean Patent Application No. 10-2015-0154910, filed on Nov. 5, 2015, in the Korean Intellectual Property Office, the entire contents of which are incorporated herein by reference in its entirety.

BACKGROUND

1. Field

Example embodiments relate to a method and/or apparatus for training an algorithm For example, at least one example embodiment relates to a method of training an algorithm to recognize a walking state of a user.

2. Description of the Related Art

With the onset of rapidly aging societies, many people may experience inconvenience and/or pain from joint problems. Thus, there may be growing interest in walking assistance apparatuses that may enable the elderly and/or patients having joint problems to walk with less effort. Furthermore, walking assistance apparatuses for intensifying muscular strength of human bodies may be useful for military purposes.

Walking assistance apparatuses may assist walking by providing an assistance force to legs of a user. Walking assistance apparatuses may recognize a walking state of the user and may provide the user with an assistance force corresponding to the recognized walking state. Because walking assistance apparatuses may need to accurately recognize a walking state to provide a proper assistance force corresponding to the walking state, research is being conducted on various methods for increasing a recognition rate of a walking state.

SUMMARY

Some example embodiments relate to method for training an algorithm to recognize a walking state of a user.

In some example embodiments, the method includes generating virtual sensing data associated with walking of a virtual human model through a dynamic simulation; and training the algorithm to recognize the walking state based on the virtual sensing data.

In some example embodiments, the generating comprises: generating the virtual human model based on a physical characteristic of a virtual human body; generating a walking model based on the virtual human model and walking environment information; and performing the dynamic simulation based on the walking model to generate the virtual sensing data.

In some example embodiments, the generating further comprises: associating a virtual sensor to a portion of the virtual human model; and generating the virtual sensing data via the virtual sensor.

In some example embodiments, the virtual sensing data includes at least one of a joint angle, walking speed data, walking acceleration data, a ground reaction force and an electromyographic (EMG) signal of the virtual human model.

In some example embodiments, the algorithm is a deep neural network (DNN).

In some example embodiments, the DNN is one of a deep convolutional neural network (DCNN) and a deep belief network (DBN).

In some example embodiments, the training comprises: calculating a probability value of each of a plurality of walking states using the algorithm based on the virtual sensing data; calculating an error value based on the probability value and a label of dynamic simulation data; and adjusting at least one parameter of the algorithm to reduce the error value.

In some example embodiments, the training further comprises: iteratively training the algorithm until the error value is equal to or less than a threshold value.

In some example embodiments, the calculating the probability value comprises: generating an input vector based on the virtual sensing data; extracting a feature element from the input vector; downsampling the input vector; and calculating the probability value based on the feature element and the downsampled input vector.

In some example embodiments, the method further comprises: encoding the virtual sensing data using the algorithm to generate compressed information; decoding the compressed information to generate decoded information; calculating an error value between the virtual sensing data and the decoded information; and adjusting at least one parameter of the algorithm based on the error value.

In some example embodiments, the calculating the error value comprises: calculating one of a Euclidean distance and a cross entropy between the virtual sensing data and the decoded information.

In some example embodiments, the method further comprises: adjusting the algorithm based on real sensing data.

In some example embodiments, the adjusting the algorithm comprises: transmitting the adjusted algorithm to an external terminal; receiving the real sensing data from the external terminal; and adjusting the algorithm based on the real sensing data.

In some example embodiments, the external terminal is a wearable device.

In some example embodiments, the external terminal is a walking assistance apparatus.

In some example embodiments, the adjusting the algorithm comprises: generating real sensing data associated with walking of a person using a sensor; and adjusting the algorithm based on the real sensing data.

In some example embodiments, the real sensing data includes at least one of a joint angle, walking speed data, walking acceleration data, a ground reaction force and an EMG signal of the person.

Some example embodiments relate to a non-transitory computer-readable storage medium storing a program for causing a processor to train an algorithm to recognize a walking state of a user.

Some example embodiments relate to an algorithm training apparatus.

In some example embodiments, the algorithm training apparatus comprises: a processor configured to, generate virtual sensing data associated with walking of a virtual human model through a dynamic simulation, and train an algorithm to recognize a walking state of a user based on the virtual sensing data; and a memory configured to store the algorithm.

Some example embodiments relate to a method of adjusting an algorithm.

In some example embodiments, the method comprises: acquiring the algorithm, the algorithm trained to recognize a walking state of a user based on virtual sensing data, the virtual sensing data representing walking of a virtual human model through a dynamic simulation; generating real sensing data associated with a walking of a user using a sensor; and adjusting the algorithm based on the real sensing data.

In some example embodiments, the algorithm is a deep neural network (DNN).

In some example embodiments, the DNN is one of a deep convolutional neural network (DCNN) and a deep belief network (DBN).

In some example embodiments, the generating the real sensing data comprises: generating the real sensing data by a sensor of a terminal associated with the user.

In some example embodiments, the terminal is a wearable device.

In some example embodiments, the terminal is a walking assistance apparatus.

In some example embodiments, the real sensing data includes at least one of a joint angle, walking speed data, walking acceleration data, a ground reaction force and an electromyographic (EMG) signal of the user.

Some example embodiments relate to a non-transitory computer-readable storage medium storing a program for causing a processor to adjust an algorithm.

Some example embodiments relate to an algorithm adjusting apparatus.

In some example embodiments, the algorithm adjusting apparatus includes a memory configured to store an algorithm trained to recognize a walking state of the user based on virtual sensing data, the virtual sensing data representing walking of a virtual human model through a dynamic simulation; a sensor configured to generate real sensing data associated with a walking of a user; and a processor configured to adjust the algorithm based on the real sensing data.

Some example embodiments relate to a controller.

In some example embodiments, the controller comprises a processor and a memory, the memory containing computer readable code that, when executed by the processor, configures the processor to, obtain virtual sensing data associated with a virtual user in a dynamic simulation, train a neural network algorithm to recognize a walking state of a user based on the virtual sensing data, receive, from one or more sensors real sensing data associated with a user walking in an environment, and adjust the neural network algorithm based on real sensing data.

In some example embodiments, the virtual sensing data includes at least one of a joint angle, walking speed data, walking acceleration data, a ground reaction force and an electromyographic (EMG) signal of the virtual user.

In some example embodiments, the neural network algorithm is a deep neural network algorithm having a plurality of cascaded processing layers therein connected in such that each successive layer uses an output from a previous layer as an input thereto.

In some example embodiments, the computer readable code, when executed, further configures the processor to train the neural network algorithm by, calculating an error in the virtual sensing data using one of an unsupervised learning task in which the virtual sensing data is unlabeled and a supervised learning task in which the virtual sensing data is labeled, and adjusting, via back-propagation, a parameter of the neural network algorithm, to reduce the error below a threshold.

In some example embodiments, the computer readable code, when executed, further configures the processor to recognize a walking state of a user using the real sensing data and a neural network algorithm trained using virtual sensing data.

Some example embodiments relate to a walking assistance apparatus.

In some example embodiments, the walking assistance apparatus comprises: a driver configured to generate an assistance torque to assist a user with walking; one or more sensors configured to sense real sensing data; and a controller configured to recognize a walking state of a user using the real sensing data and a neural network algorithm trained using virtual sensing data, and instruct the driver to generate the assistance torque based on the walking state.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 13 is a flowchart illustrating an operation of adjusting an algorithm based on real sensing data in the algorithm adjusting method of FIG. 12.

DETAILED DESCRIPTION

Figure 1:
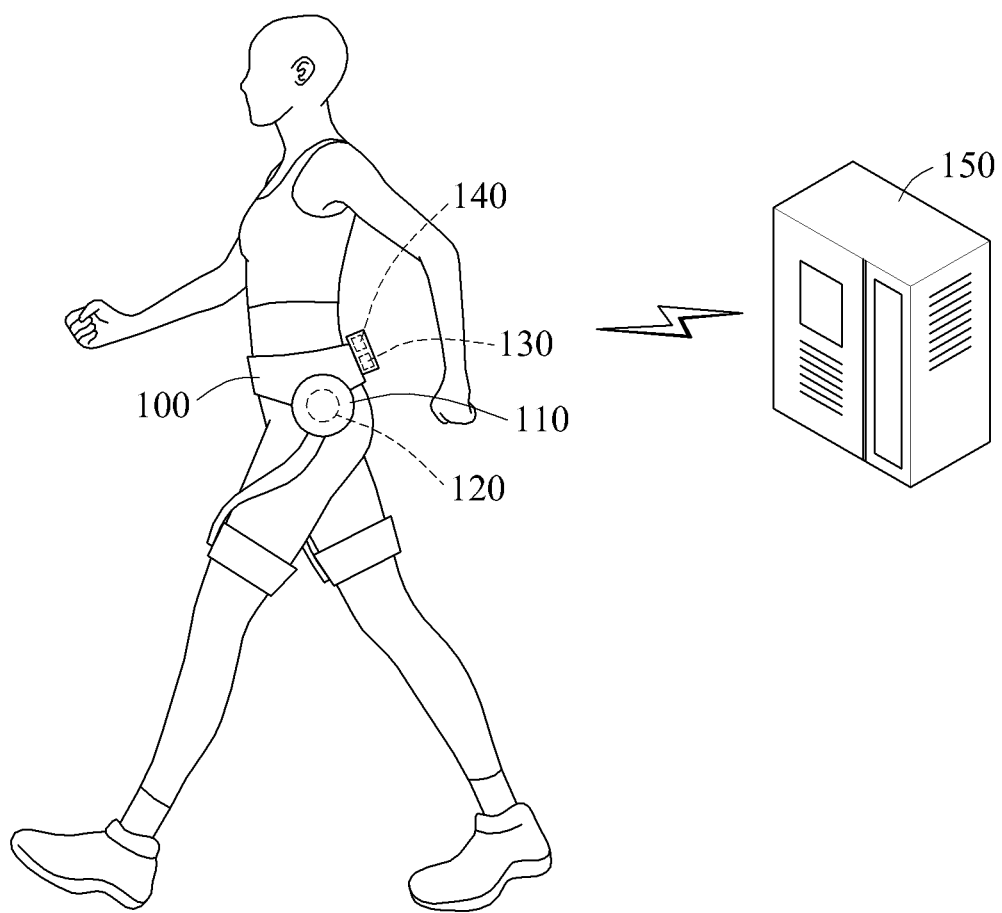
FIGS. 1 and 2 illustrate a walking assistance apparatus according to at least one example embodiment.

Hereinafter, some example embodiments will be described in detail with reference to the accompanying drawings. The scope of the patent application, however, should not be construed as limited to the embodiments set forth herein. Like reference numerals in the drawings refer to like elements throughout the present disclosure.

Various modifications may be made to the example embodiments. However, it should be understood that these embodiments are not construed as limited to the illustrated forms and include all changes, equivalents or alternatives within the idea and the technical scope of this disclosure.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which these example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

<Summary of Walking Assistance Apparatus>

Figure 2:
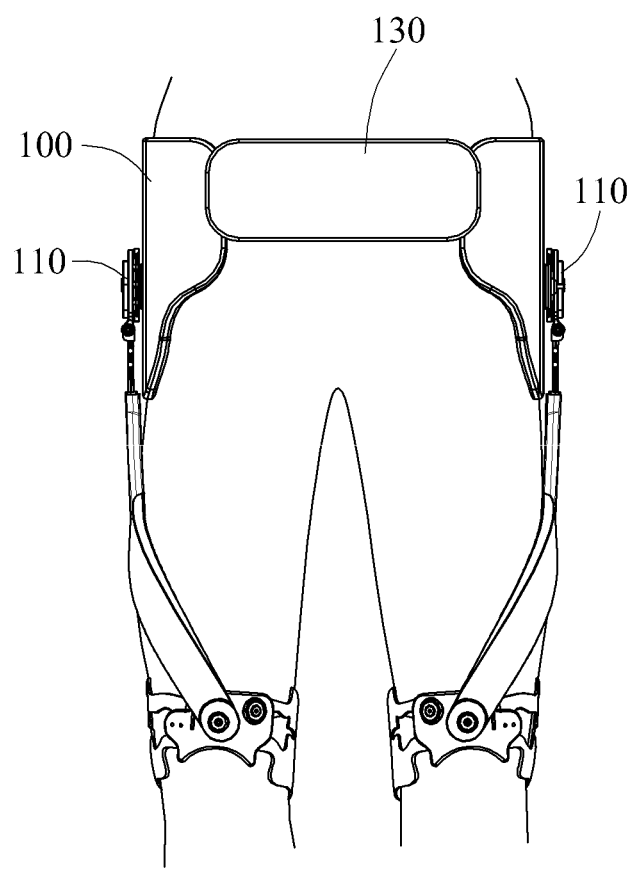

FIGS. 1 and 2 illustrate a walking assistance apparatus according to at least one example embodiment.

Referring to FIG. 1, a walking assistance apparatus 100 may assist walking of a user. The walking assistance apparatus 100 may be a wearable device. FIG. 1 illustrates an example of a hip-type walking assistance apparatus, however, a type of walking assistance apparatuses is not limited to the hip-type walking assistance apparatus. Accordingly, the walking assistance apparatus 100 may be, for example, one of a walking assistance apparatus for supporting a portion of a pelvic limb, a walking assistance apparatus for supporting up to a knee, and a walking assistance apparatus for supporting up to an ankle, and a walking assistance apparatus for supporting an entire pelvic limb.

Referring to FIG. 1, the walking assistance apparatus 100 may include a driving portion 110, a sensor 120, an inertial measurement unit (IMU) sensor 130, and a controller 140.

The driving portion 110 may output a driving force and assist a movement of a hip joint of a user. The driving portion 110 may be located on, for example, a right hip portion and/or a left hip portion of the user. The driving portion 110 may include a motor to generate a rotational torque.

The sensor 120 may measure hip joint angles of the hip joints of the user while the user is ambulatory. Information about the hip joint angles sensed by the sensor 120 may include, for example, an angle of a right hip joint, an angle of a left hip joint, a difference between both the hip joint angles, and a direction of motion for a hip joint. The sensor 120 may be located in, for example, the driving portion 110.

The sensor 120 may include a potentiometer. The potentiometer may sense a right (R)-axis joint angle, a left (L)-axis joint angle, an R-axis joint angular velocity, and an L-axis joint angular velocity, based on a gait motion of the user.

The IMU sensor 130 may measure acceleration information and posture information while the user is ambulatory. For example, the IMU sensor 130 may sense an x-axis acceleration, a y-axis acceleration, a z-axis acceleration, an x-axis angular velocity, a y-axis angular velocity, and a z-axis angular velocity, based on a gait motion of the user.

The walking assistance apparatus 100 may detect a point at which a foot of the user lands based on the acceleration information measured by the IMU sensor 130. A pressure sensor (not shown) may be attached to a sole of the user, and may detect a point in time at which a foot of the user lands. A force sensor (not shown) may be attached to a sole of the user, and may measure a ground reaction force.

The walking assistance apparatus 100 may include, in addition to the above-described sensor 120 and IMU sensor 130, another sensor (for example, an electromyography (EMG) sensor) configured to sense a change in a biosignal or a quantity of motion of a user based on a gait motion.

The controller 140 may include a communication device, and may communicate with an external server 150 using the communication device. The controller 140 may exchange data with the server 150. For example, controller 140 may exchange data with the server 150 via the Internet.

The communication device may include transmitters and/or receivers. The transmitters may include hardware and any necessary software for transmitting signals including, for example, data signals and/or control signals. The receivers may include hardware and any necessary software for receiving signals including, for example, data signals and/or control signals from one or more sensors.

The controller 140 may control the driving portion 110 to output an assistance force to assist walking of the user. For example, the controller 140 may output a control signal to control the driving portion 110 to generate a torque. The driving portion 110 may generate a torque based on the control signal output from the controller 140.

The controller 140 may use an algorithm to calculate a torque generated by the driving portion 110. The algorithm may be, for example, a deep neural network (DNN). The DNN may be either a deep convolutional neural network (DCNN) or a deep belief network (DBN).

The controller 140 may recognize a walking state of a user wearing the walking assistance apparatus 100 using the algorithm. For example, the walking state may include a type of activities of the user, a type of gait-related diseases and/or a walking environment. The activity of the user may include, for example, a normal gait, a low-speed gait or running. The gait-related diseases may include, for example, a stroke or a Parkinson's disease. The walking environment may include, for example, a level surface, stairs and a direction of a slope of a ground.

To accurately recognize a walking state among a plurality of walking states based on basic data associated with walking states, the algorithm may need to recognize or determine that an input of the basic data indicates the walking state. To increase the above recognition rate, the algorithm may be trained or learned based on the basic data. Training of the algorithm may be deep learning.

<Algorithm Training Apparatus>

Figure 3:
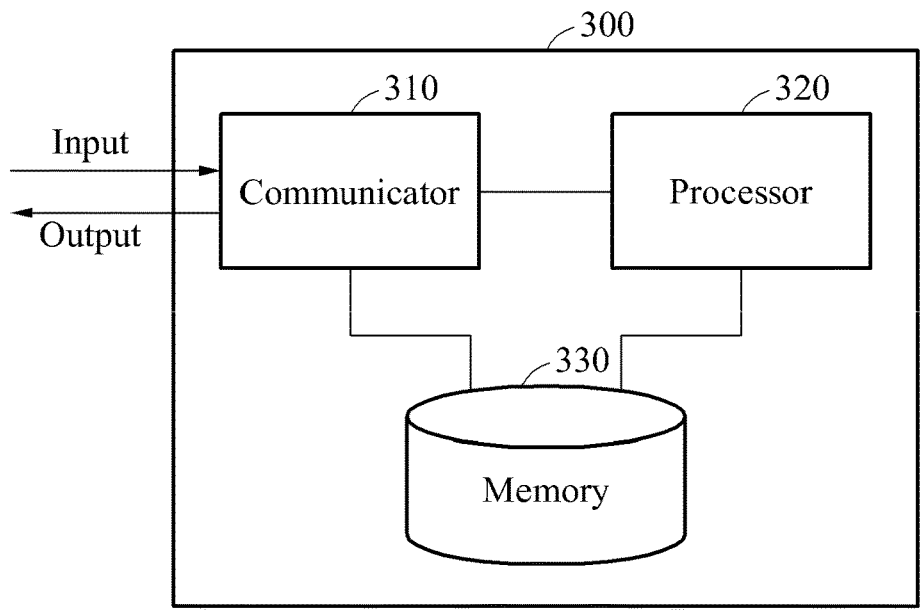
FIG. 3 illustrates a configuration of an algorithm training apparatus according to at least one example embodiment.

FIG. 3 illustrates a configuration of an algorithm training apparatus according to at least one example embodiment.

Referring to FIG. 3, in some example embodiments, an algorithm training apparatus 300 may be included in the walking assistance apparatus 100. The algorithm training apparatus 300 may include the controller 140. In another example embodiment, the algorithm training apparatus 300 may be included in the server 150. When the algorithm training apparatus 300 is included in the server 150, a trained algorithm may be stored in a memory of the walking assistance apparatus 100, and the controller 140 may load the stored algorithm.

The algorithm training apparatus 300 may include a communicator 310, a processor 320 and a memory 330.

The communicator 310 may exchange data or information with devices of the walking assistance apparatus 100 or devices of the server 150.

The communicator 310 may include transmitters and/or receivers. The transmitters may include hardware and any necessary software for transmitting signals including, for example, data signals and/or control signals. The receivers may include hardware and any necessary software for receiving signals including, for example, data signals and/or control signals from one or more sensors.

The processor 320 may process data received by the communicator 310 and data stored in the memory 330. For example, the processor 320 may include the controller 140.

The processor 320 may be implemented by at least one semiconductor chip disposed on a printed circuit board. The processor 320 may be an arithmetic logic unit, a digital signal processor, a microcomputer, a field programmable array, a programmable logic unit, a microprocessor or any other device capable of responding to and executing instructions in a defined manner.

The memory 330 may store data received by the communicator 310 and data processed by the processor 320.

The memory 330 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

Figure 4:
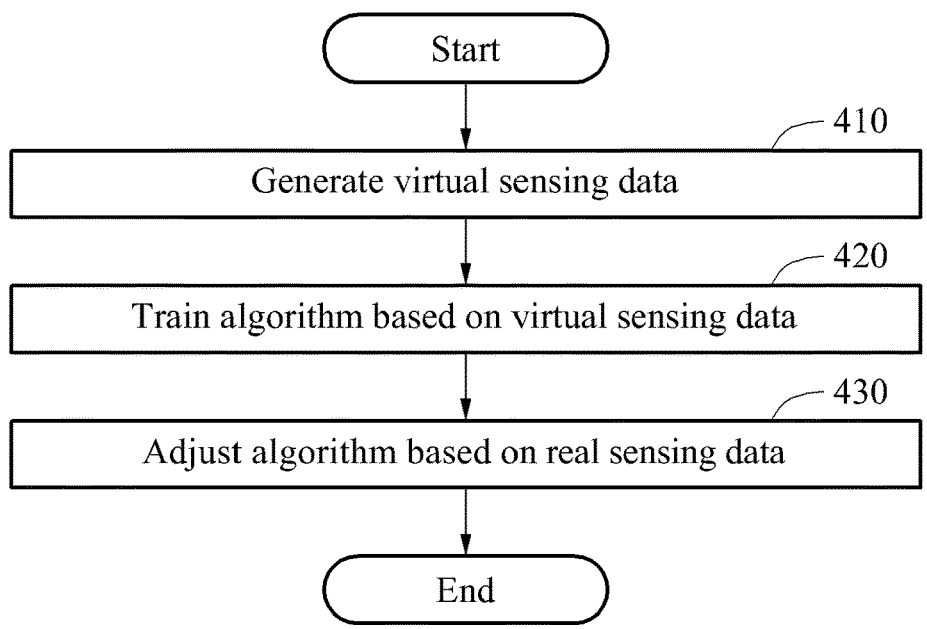
FIG. 4 is a flowchart illustrating an algorithm training method according to at least one example embodiment.

FIG. 4 is a flowchart illustrating an algorithm training method according to at least one example embodiment.

Referring to FIG. 4, in operation 410, the processor 320 may generate virtual sensing data associated with walking of a virtual human model through a dynamic simulation. The virtual sensing data may be used as basic data to train an algorithm. When the virtual sensing data is generated, costs and resources required to acquire data to train the algorithm may be reduced as compared to only utilizing non-virtual real data for training.

In operation 420, the processor 320 may train the algorithm based on the virtual sensing data. The training of the algorithm may indicate adjusting a value of at least one parameter included in the algorithm. By training the algorithm, a recognition rate to recognize a walking state of a user may increase. The training of the algorithm based on the virtual sensing data may be referred to as "pre-training." The processor 320 may train the algorithm based on a deep learning scheme. Examples of the deep learning schemes are discussed in more detail below with regards to the supervised learning scheme of FIG. 6 and the unsupervised learning scheme of FIG. 8.

In an example embodiment, when operation 430 is performed by the server 150, the processor 320 may be understood to perform operation 430. In another example embodiment, operation 430 may be understood to be performed by the walking assistance apparatus 100. In the following description, operation 430 may be performed by the processor 320, however, there is no limitation thereto.

In operation 430, the processor 320 may adjust the algorithm based on real sensing data. The real sensing data may be data measured by the sensor 120 and the IMU 130 in the walking assistance apparatus 100. By adjusting the algorithm based on real sensing data, a recognition rate of the algorithm may increase. The adjusting of the algorithm based on the real sensing data may be referred to as "fine-tuning." The adjusting of the algorithm based on the real sensing data may be a personalization of the walking assistance apparatus 100. Examples of fine-tuning the algorithm are discussed in more detail below with regards to FIGS. 9 and 10.

Figure 5:
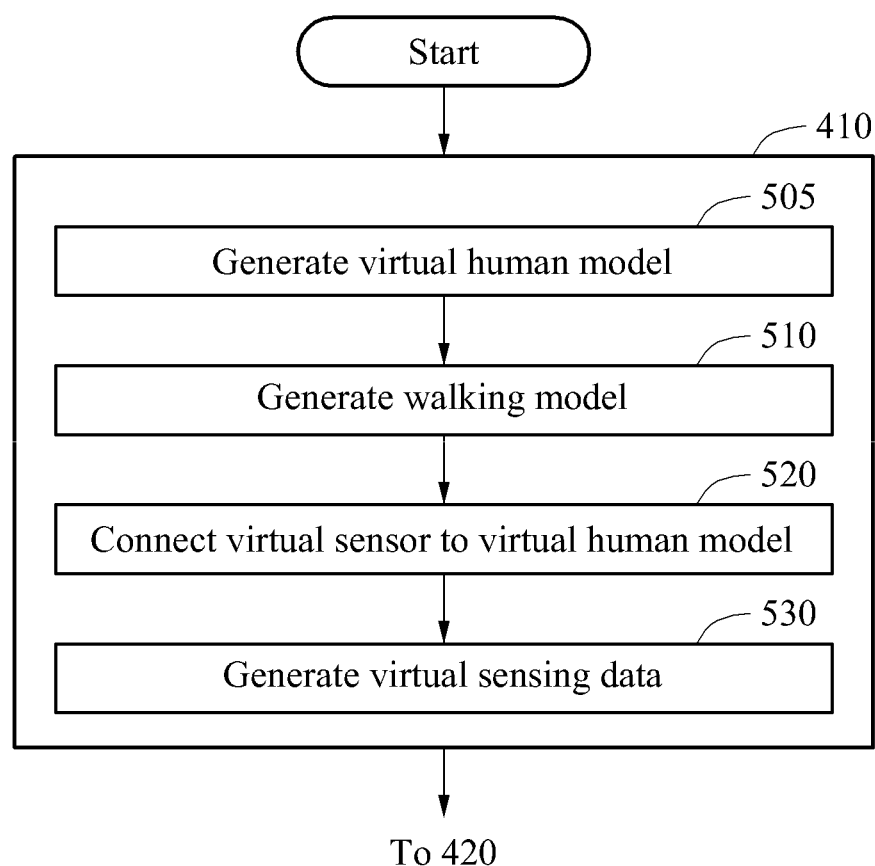
FIG. 5 is a flowchart illustrating an operation of generating virtual sensing data in the algorithm training method of FIG. 4.

FIG. 5 is a flowchart illustrating operation 410 in the algorithm training method of FIG. 4.

Referring to FIGS. 4 and 5, when performing operation 410 of FIG. 4, the processor 320 may perform operations 505 through 530 of FIG. 5.

In operation 505, the processor 320 may generate the virtual human model based on a physical characteristic of a virtual human body received from the user. The physical characteristic may include, for example, a height, a weight or a gender of the virtual human body. The user may diversify virtual human models generated by setting different physical characteristics. For example, virtual human models for children, adults and elders may be generated based on physical characteristics.

In operation 510, the processor 320 may generate a walking model based on the virtual human model and walking environment information. The walking environment information may include, for example, information about a ground where the virtual human model walks, a walking speed or a type of diseases. When the same virtual human models are generated but different walking environments are set, various walking models may be generated.

In operation 520, the processor 320 may connect a virtual sensor to the virtual human model. A user may designate a location in which the virtual sensor is connected to the virtual human model, and a type of the virtual sensor.

The virtual sensor may measure information about kinesiology and kinematics, a ground reaction force and an EMG from the virtual human model. For example, the virtual sensor may measure an acceleration, a speed, a joint angle, a joint angular velocity, a ground reaction force and an EMG of a part of the virtual human body.

In operation 530, the processor 320 may generate the virtual sensing data by performing the dynamic simulation on the virtual human model. For example, the processor 320 may perform the dynamic simulation using a physical engine. The virtual sensing data may be generated by the virtual sensor, and may include at least one of a joint angle, walking speed data, walking acceleration data, ground reaction force data and an electromyographic (EMG) signal of the virtual human model.

The virtual sensing data may include primary data measured directly using the virtual sensor, and secondary data calculated based on the primary data. The secondary data may include, for example, a stride length, a stride rate and a cadence of a user. The processor 320 may calculate the secondary data by processing the primary data.

Because various virtual human models and various walking environments are set based on input conditions, virtual sensing data generated based on a walking model may change based on the walking model. It is possible to easily acquire a large quantity of data to train an algorithm through the dynamic simulation.

Figure 6:
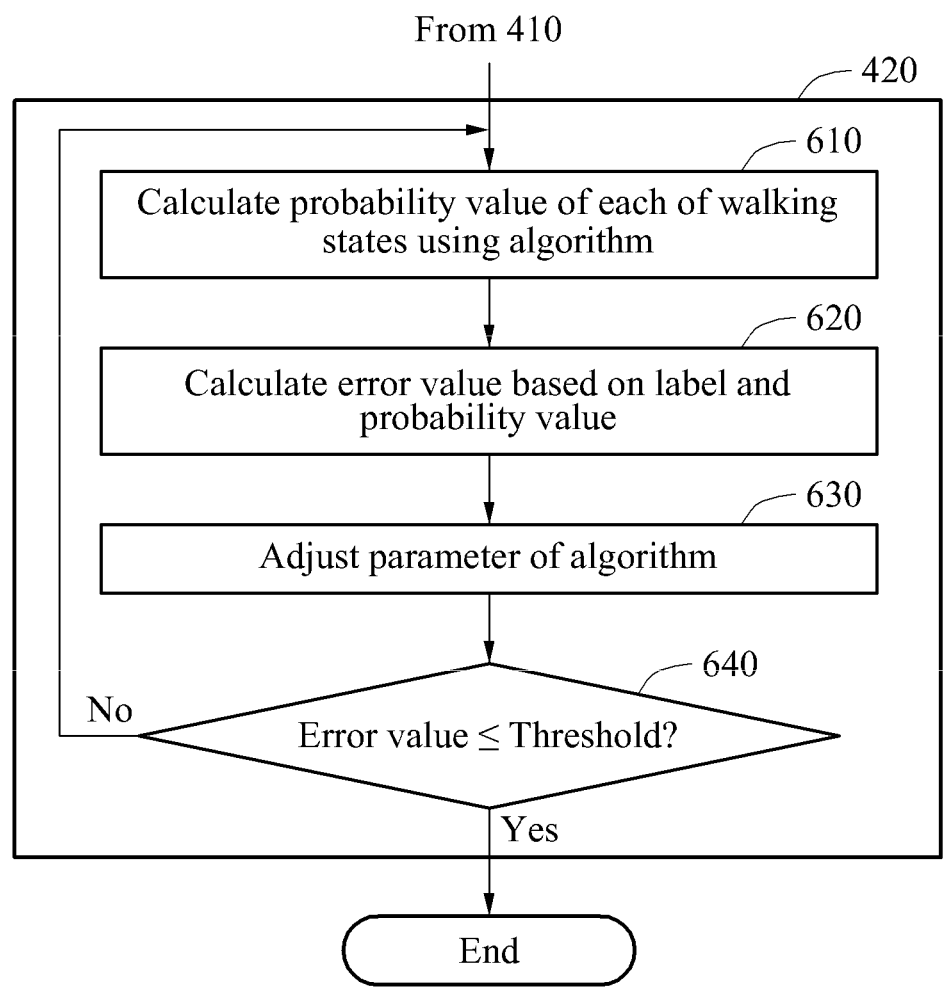
FIG. 6 is a flowchart illustrating an example of an operation of training an algorithm based on virtual sensing data in the algorithm training method of FIG. 4.

FIG. 6 is a flowchart illustrating an example of operation 420 in the algorithm training method of FIG. 4.

Referring to FIGS. 4 and 6, in some example embodiments, when performing operation 420 of FIG. 4, the processor 320 may perform operations 610 through 640 of FIG. 6. Operations 610 through 640 may correspond to a supervised learning scheme.

In operation 610, the processor 320 may calculate a probability value of each of preset walking states using the algorithm based on the virtual sensing data. When operation 610 is performed first, each of parameters in the algorithm may be set to have a default value. The walking states may refer to classes recognized based on sensed data. The walking states may include a type of activities of a user, a type of gait-related diseases and a walking environment.

For example, when the walking states include a level walking state, a downhill walking state, an uphill walking state and a stair walking state, the processor 320 may calculate, based on virtual sensing data, a probability that a walking state is the level walking state, a probability that a walking state is the downhill walking state, a probability that a walking state is the uphill walking state and a probability that a walking state is the stair walking state. In this example, the virtual sensing data may represent the walking state.

In operation 620, the processor 320 may calculate an error value based on the probability value and a label of dynamic simulation data. The label may be a physical characteristic of a virtual human body and walking environment information. For example, when the label indicates a level surface, and when a probability of a level surface, a probability of a downhill, a probability of an uphill and a probability of stairs are calculated as "0.3," "0.2," "0.3" and "0.2," respectively, an error value may be calculated as "0.7."

In operation 630, the processor 320 may adjust at least one parameter of the algorithm based on the calculated error value. For example, the processor 320 may use a gradient descent scheme to adjust the parameter. The adjusting of the parameter may be back-propagation of the algorithm. In the back-propagation, the processor 320 may calculate the gradient of a loss function with respect to all the weights in the network. The processor 320 may use the gradient to update the weights, in an attempt to minimize the loss function.

In operation 640, the processor 320 may compare the error value with a threshold. The threshold may be set in advance. When the error value is equal to or less than the threshold, the processor 320 may terminate the training of the algorithm. When the error value exceeds the threshold, the processor 320 may re-perform operations 610 through 630. In other words, the processor 320 may iteratively perform operation 420 until the error value is equal to or less than the threshold.

Figure 7:
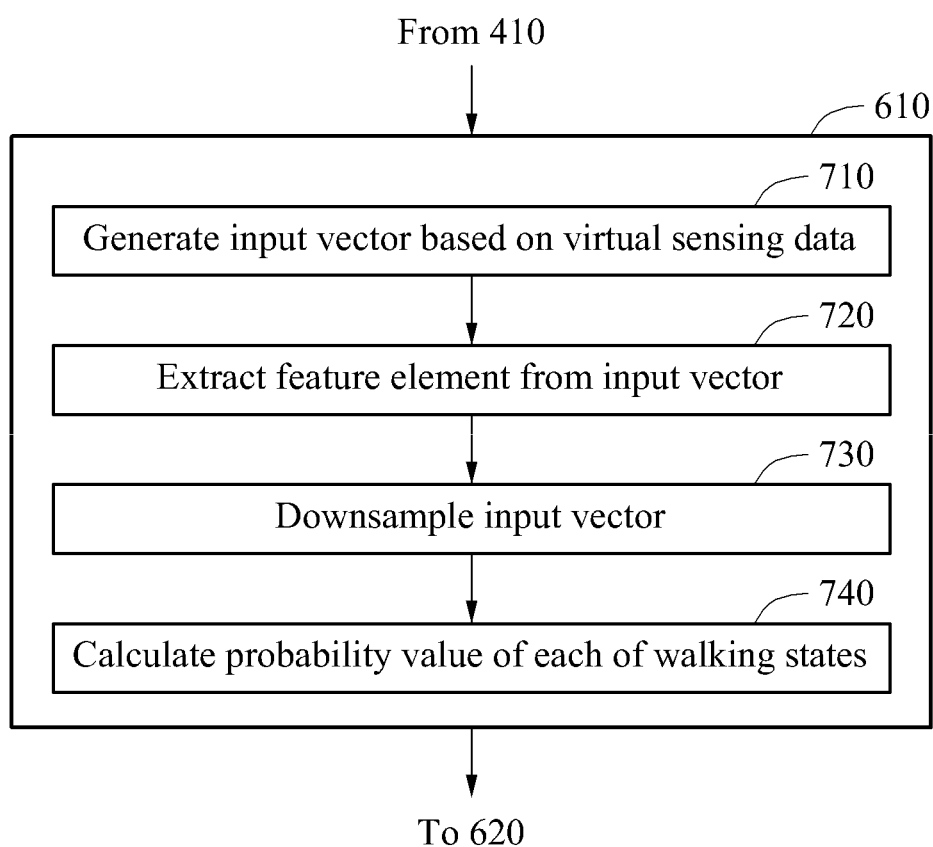
FIG. 7 is a flowchart illustrating an operation of calculating a probability value of each of walking states in the operation of FIG. 6.

FIG. 7 is a flowchart of operation 610 of FIG. 6.

Referring to FIGS. 6 and 7, when performing operation 610 of FIG. 6, the processor 320 may perform operations 710 through 740 of FIG. 7.

In operation 710, the processor 320 may generate an input vector based on the virtual sensing data. The processor 320 may add sensor noise to the virtual sensing data. The sensor noise may be, for example, white Gaussian noise. The virtual sensing data to which the sensor noise is added may be fake sensing data. For example, the processor 320 may generate a single input vector based on virtual sensing data corresponding to a desired (or, alternatively, a predetermined) time. Input vectors may be generated for each channel of the virtual sensor, and may be generated to include a plurality of channels. In an example, the input vector may include a walking speed, a joint angle and a joint angular velocity. In another example, the input vector may include an x-axis value, a y-axis value and a z-axis value of a joint angular velocity.

When the algorithm is a neural network, operation 710 may correspond to a data layer. The processor 320 may extract data and a label from a database file or a database in which virtual sensing data is stored.

In operation 720, the processor 320 may extract a feature element from the input vector. For example, the processor 320 may perform a convolution operation of the input vector and a kernel vector, and may extract the feature element. The kernel vector may be a filter of a preset size. The feature element y may be extracted using Equation 1 shown below.

$$y = f(b + \Sigma k * x) \qquad \text{[Equation 1]}$$

In Equation 1, x denotes the input vector, k denotes the kernel vector, b denotes a bias vector, and y denotes the feature element. Also, f denotes a non-linear mapping function, and may be, for example, a hyperbolic tangent function.

When the algorithm is a neural network, operation 720 may correspond to a convolutional layer. At least one convolutional layer may be provided. For example, when a single convolutional layer is provided, a single input vector and a single feature element may be generated. In another example, when a plurality of convolutional layers are provided, a plurality of input vectors and a plurality of feature elements may be generated. The plurality of convolutional layers may be processed in parallel. The plurality of convolutional layers may be understood as a plurality of channels, and data of each of the channels may be processed by each of the convolutional layers. When virtual sensor data is processed for each of channels, data with different characteristics may be independently learned.

In operation 730, the processor 320 may downsample the input vector.

In some example embodiments, to down sample the input vector y, the processor 320 may select a sample with a maximum value among a preset number of samples of the input vector, using Equation 2 shown below.

$$y = \max_{r \times s}(x) \qquad \text{[Equation 2]}$$

In Equation 2, "r×s" denotes the preset number of the samples of the input vector, and may correspond to a desired (or, alternatively, a predetermined) region. Also, max(x) denotes a function to select a sample with a maximum value among samples in a predetermined region, and y denotes the sample with the maximum value.

In other example embodiments, to downsample the input vector y, the processor 320 may select a sample with a mean value among the preset number of the samples of the input vector, using Equation 3 shown below.

$$y = \text{mean}_{r \times s}(x) \qquad \text{[Equation 3]}$$

In Equation 3, x denotes the input vector, and mean(x) denotes a function to select a sample with a mean value among samples in a predetermined region. Also, y denotes the sample with the mean value.

When the algorithm is a neural network, operation 730 corresponds to a pooling layer. At least one pooling layer may be provided. In an example, when a single convolutional layer is provided, a single pooling layer may be provided. In another example, when a plurality of convolutional layers are provided, a plurality of pooling layers may be provided. The plurality of pooling layers may be processed in parallel.

The processor 320 may alternately perform operations 720 and 730 multiple times.

In operation 740, the processor 320 may calculate a probability value of each of the walking states based on the feature element and the downsampled input vector.

The processor 320 may calculate an output vector using Equation 4 shown below.

$$y = g(b1 + Wx) \quad \text{[Equation 4]}$$

In Equation 4, x denotes the input vector, W denotes a weight matrix vector, and b1 denotes a bias vector. Also, g(x) denotes an activation function, and may be represented as shown in Equation 5, for example.

$$g(x) = \text{sigmoid}(1/(1+e^{-x})) \quad \text{[Equation 5]}$$

When the algorithm is a neural network, a process of calculating an output vector may correspond to a fully-connected neural network layer. The fully-connected neural network layer may be a hidden layer. The hidden layer may be fully connected to at least one pooling layer. When virtual sensor data is processed for each of channels, characteristics that are independently learned may be integrated in the hidden layer.

The processor 320 may calculate a probability value of each of preset walking states based on the output vector. The probability value may be calculated using Equation 6 shown below.

$$O(a) = \left[ \frac{\exp(a_1)}{\sum_{i=1}^{n} \exp(a_i)}, \cdots, \frac{\exp(a_n)}{\sum_{i=1}^{n} \exp(a_i)} \right] \quad \text{[Equation 6]}$$

Due to a variety of walking states, the walking states may be classified into similar types and distinguished from each other. For example, walking states may be classified into a class associated with a walking speed, a class associated with diseases, and a class associated with a state of a ground. The processor 320 may calculate a probability value of each of the walking states for each of the classes.

In Equation 6, a denotes a desired (or, alternatively, a predetermined) class, and a1 through an denote walking states included in the class a. Also, exp(ai) denotes an expected value of the walking state ai, and O(a) denotes a probability value of each of the walking states a1 through an included in the class a.

For example, when the class a is associated with a state of a ground, and when the walking states a1, a2, a3 and a4 correspond to a level surface, a downhill, an uphill and stairs, respectively, probability values O(a) may be calculated as "0.5," "0.2," "0.2" and "0.1," respectively. In this example, because the walking state a1 has a highest probability, the state of the ground may be recognized as the level surface.

When the algorithm is a neural network, a process of calculating a probability value of each of walking states may correspond to a softmax layer.

Figure 8:
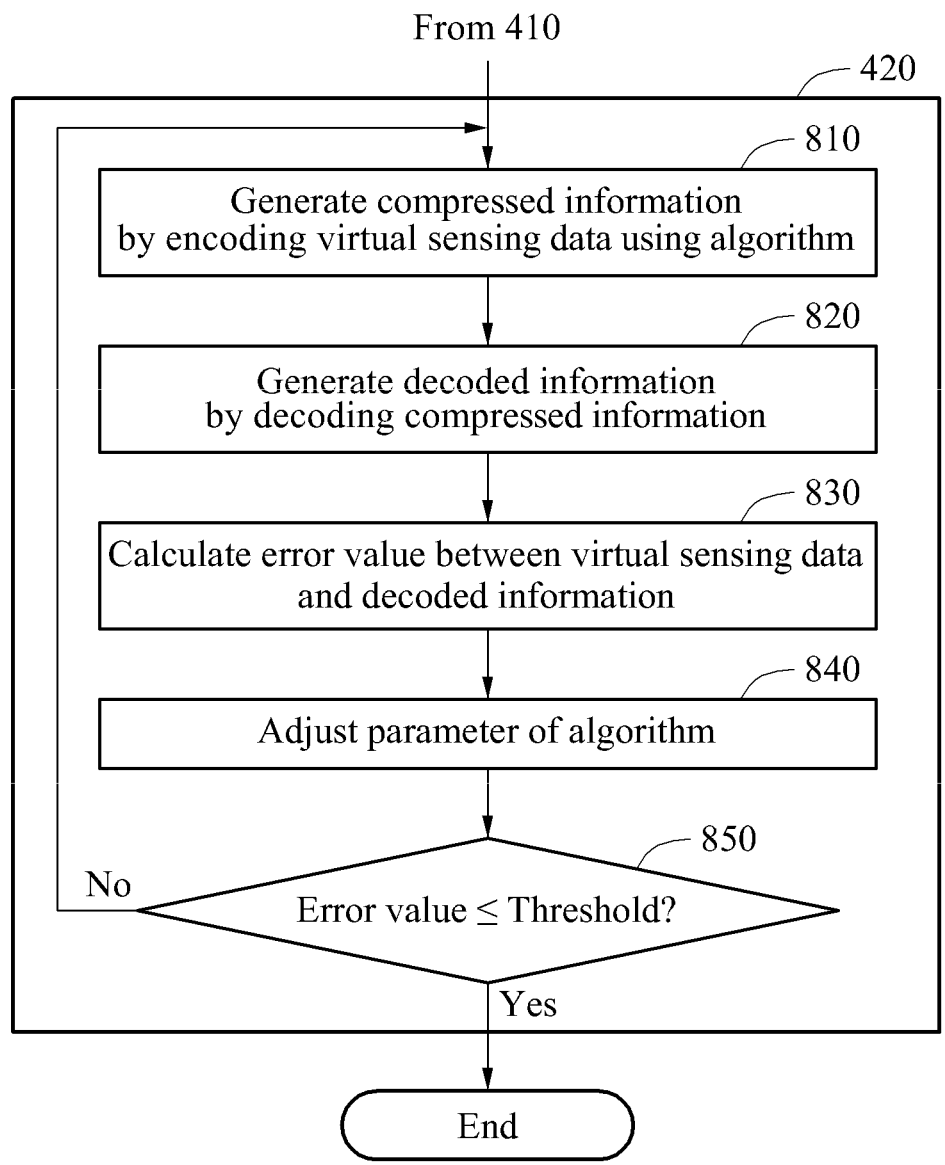
FIG. 8 is a flowchart illustrating another example of an operation of training an algorithm based on virtual sensing data in the algorithm training method of FIG. 4.

FIG. 8 is a flowchart illustrating another example of operation 420 in the algorithm training method of FIG. 4.

Referring to FIGS. 4 and 8, in other example embodiments, when performing operation 420, the processor 320 may perform operations 810 through 850 of FIG. 8. Operations 810 through 850 may correspond to an unsupervised learning scheme. The unsupervised learning scheme may be used when a label of virtual sensing data does not exist.

In operation 810, the processor 320 may generate compressed information by encoding the virtual sensing data using the algorithm. The compressed information may correspond to the output vector of operation 740. Description of a scheme of encoding the virtual sensing data may be replaced by the description of operations 710 through 740.

In operation 820, the processor 320 may generate decoded information by decoding the compressed information. The processor 320 may decode the compressed information in an inverse order to the encoding discussed with reference to FIG. 7. For example, the compressed information may be decoded in an order of a fully-connected neural network layer, a pooling layer and a convolutional layer.

In operation 830, the processor 320 may calculate an error value between the virtual sensing data and the decoded information.

In some example embodiments, the processor 320 may calculate a cross entropy between the virtual sensing data and the decoded information, to calculate the error value. The cross entropy may be calculated using Equation 7 shown below.

$$E(a) = \frac{-1}{n} * \sum_{i=1}^{n} [p_i \log(q_i) + (1-p_i)\log(1-q_i)] \quad \text{[Equation 7]}$$

In Equation 7, a denotes a desired (or, alternatively, a predetermined) class, n denotes a number of walking states included in the class a, pi denotes a value of the virtual sensing data, and qi denotes a value of the decoded information.

In other example embodiments, the processor 320 may calculate a Euclidean distance between the virtual sensing data and the decoded information, to calculate the error value.

In operation 840, the processor 320 may adjust at least one parameter of the algorithm based on the calculated error value. The adjusting of the parameter may be back-propagation of the algorithm.

In operation 850, the processor 320 may compare the error value with a threshold. The threshold may be set in advance. When the error value is equal to or less than the threshold, the processor 320 may terminate the training of the algorithm. When the error value exceeds the threshold, the processor 320 may re-perform operations 810 through 840. In other words, operation 420 may be iteratively performed until the error value is equal to or less than the threshold.

Figure 9:
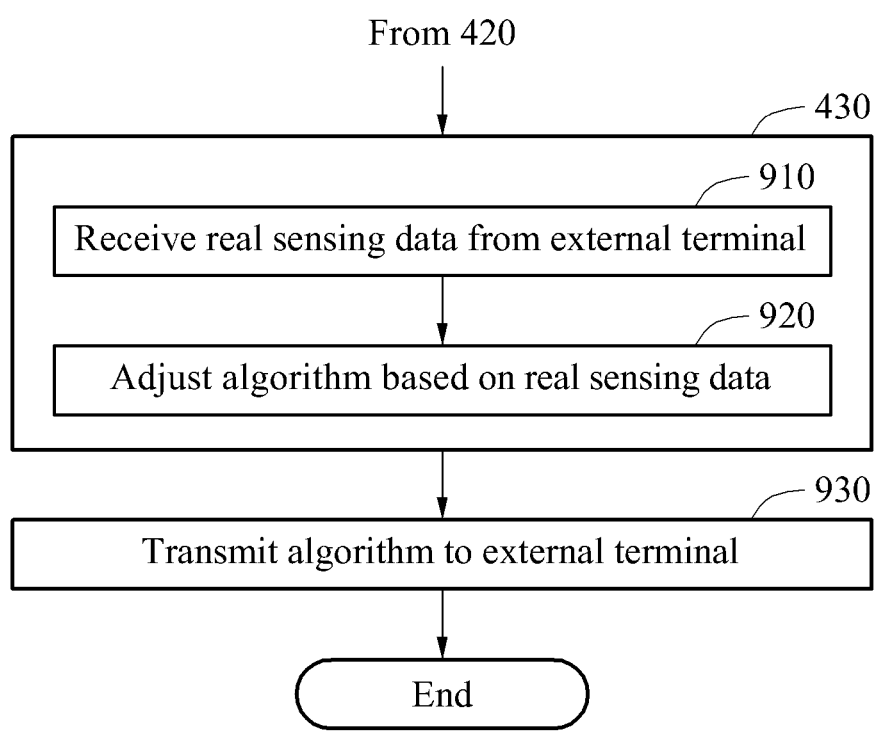
FIG. 9 is a flowchart illustrating an example of an operation of adjusting an algorithm based on real sensing data in the algorithm training method of FIG. 4.

FIG. 9 is a flowchart illustrating an example of operation 430 in the algorithm training method of FIG. 4.

When an algorithm adjusting method is performed by the server 150, operation 430 may include operations 910 and 920. Further, in some example embodiments, the algorithm adjusting method may further include operation 930.

In operation 910, the communicator 310 may receive real sensing data from an external terminal. The external terminal may be, for example, the walking assistance apparatus 100 or a wearable device. For example, the communicator 310 may receive the real sensing data from the external terminal via the Internet.

In operation 920, the processor 320 may adjust the algorithm based on the real sensing data. For example, the processor 320 may adjust the algorithm based on the real sensing data by performing the operations described above with reference to adjusting of the algorithm based on the virtual sensing data but substituting the virtual sensing data with the real sensing data, and accordingly is omitted here.

In operation 930, the communicator 310 may transmit the adjusted algorithm to the external terminal. The external terminal may recognize a walking state using the adjusted algorithm.

Figure 10:
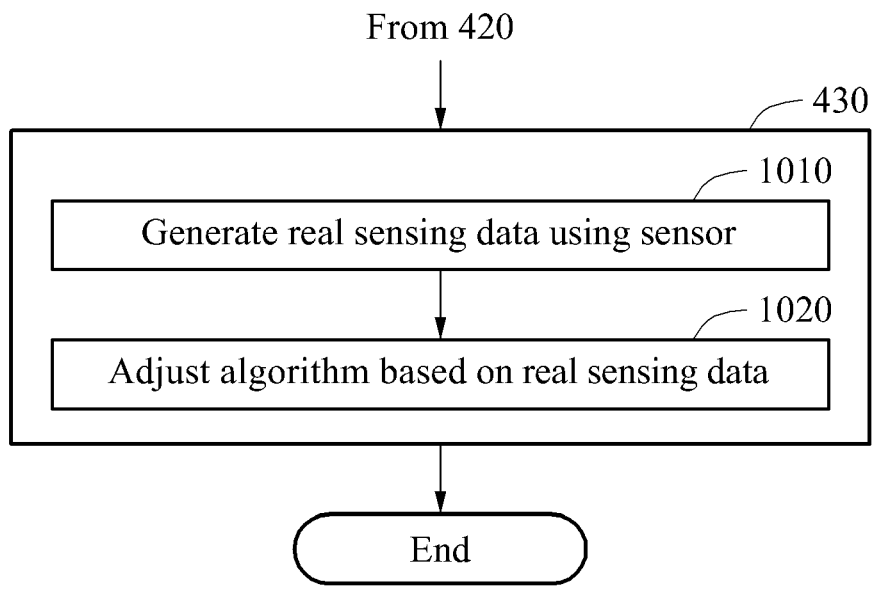
FIG. 10 is a flowchart illustrating another example of an operation of adjusting an algorithm based on real sensing data in the algorithm training method of FIG. 4.

FIG. 10 is a flowchart illustrating another example of operation 430 in the algorithm training method of FIG. 4.

For example, operations 410 through 430 may be performed by the same apparatus. In this example, operation 430 may include operations 1010 and 1020 of FIG. 10.

In operation 1010, the processor 320 may generate real sensing data using a sensor. The real sensing data may include primary data measured directly using a real sensor, and secondary data calculated based on the primary data. The secondary data may include, for example, a stride length, a stride rate and a cadence of a user.

In operation 1020, the processor 320 may adjust the algorithm based on the real sensing data.

Figure 11:
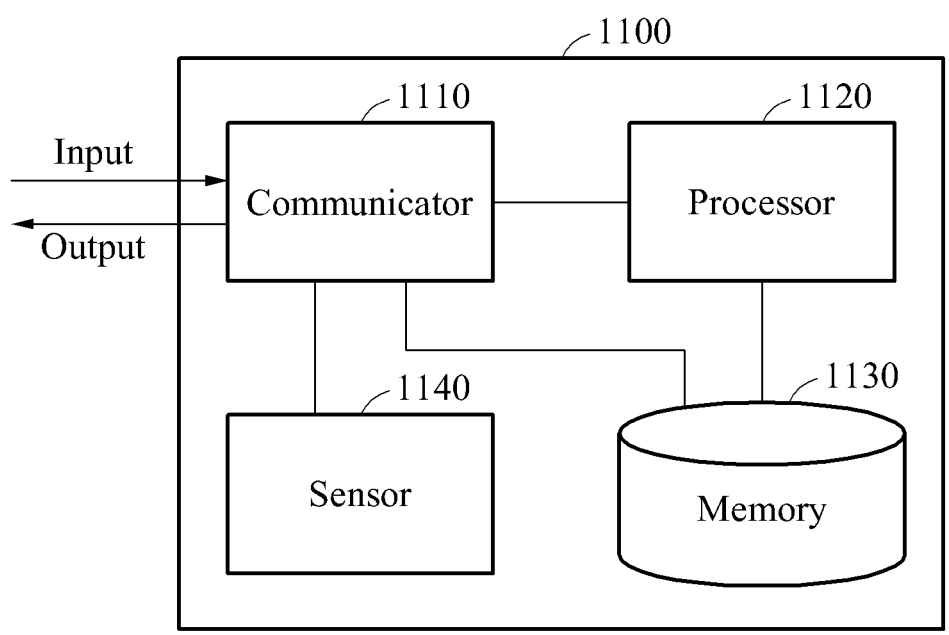
FIG. 11 illustrates a configuration of an algorithm adjusting apparatus according to at least one example embodiment.

FIG. 11 illustrates a configuration of an algorithm adjusting apparatus according to at least one example embodiment.

Referring to FIGS. 1 and 11, the walking assistance apparatus 100 may include an algorithm adjusting apparatus 1100. The algorithm adjusting apparatus 1100 may adjust an algorithm based on real sensing data. The algorithm adjusting apparatus 1100 may include a communicator 1110, a processor 1120, a memory 1130 and a sensor 1140.

The communicator 1110 may include transmitters and/or receivers. The transmitters may include hardware and any necessary software for transmitting signals including, for example, data signals and/or control signals. The receivers may include hardware and any necessary software for receiving signals including, for example, data signals and/or control signals from one or more sensors. The communicator 1110 may exchange data or information with devices in the walking assistance apparatus 100 or the server 150.

The processor 1120 may be a hardware processor. For example, the processor 1120 may be implemented by at least one semiconductor chip disposed on a printed circuit board. The processor 1120 may be an arithmetic logic unit, a digital signal processor, a microcomputer, a field programmable array, a programmable logic unit, a microprocessor or any other device capable of responding to and executing instructions in a defined manner. The processor 1120 may process data received by the communicator 1110 and data stored in the memory 1130. For example, the processor 1120 may include the controller 140.

The memory 1130 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM). The memory 1130 may store data received by the communicator 1110 and data processed by the processor 1120.

The sensor 1140 may measure information associated with walking of a user. The sensor 1140 may include the sensor 120 and the IMU 130. The sensor 1140 may measure a walking speed, a walking acceleration, a joint angle, a joint angular velocity, a ground reaction force and an EMG.

Figure 12:
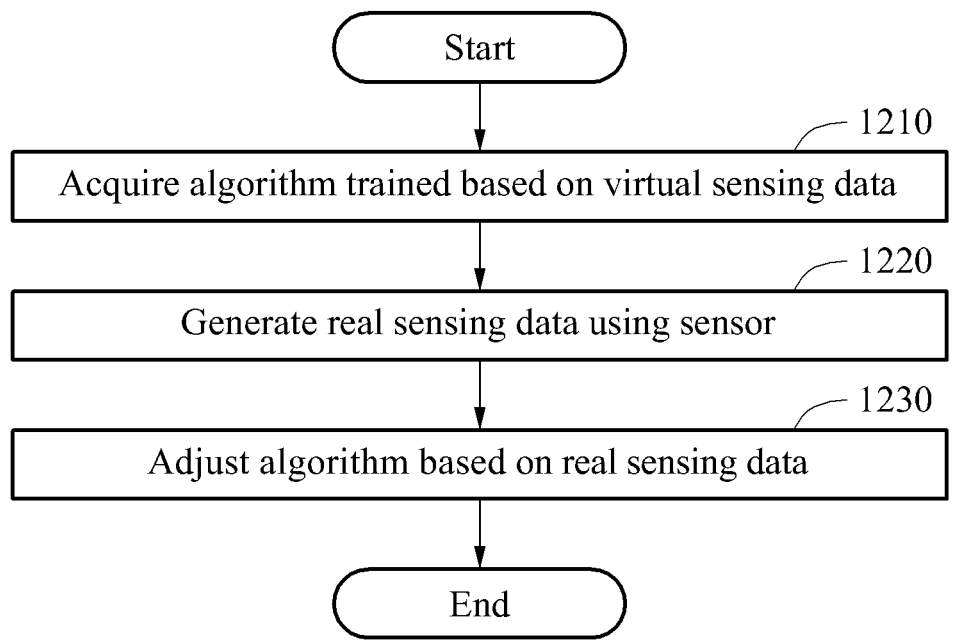
FIG. 12 is a flowchart illustrating an algorithm adjusting method according to at least one example embodiment.

FIG. 12 is a flowchart illustrating an algorithm adjusting method according to at least one example embodiment.

Referring to FIG. 12, in operation 1210, the processor 1120 may acquire an algorithm trained based on virtual sensing data. The acquired virtual sensing data be data that has been generated in association with walking of a virtual human model through a dynamic simulation, and trained based on the virtual sensing data to recognize a walking state of a user.

In an example, the processor 1120 may receive a trained algorithm from the server 150 through the communicator 1110. In another example, the processor 1120 may load an algorithm stored in the memory 1130. In still another example, when an algorithm is implemented as a chip, the processor 1120 may acquire the algorithm using the chip.

In operation 1220, the sensor 1140 may generate real sensing data. The real sensing data may be data measured by the sensor 120 and the IMU 130 in the walking assistance apparatus 100. For example, the real sensing data may include at least one of a joint angle, walking speed data, walking acceleration data, ground reaction force data and an EMG signal of a person wearing the walking assistance apparatus 100. A type of real sensing data may correspond to a type of virtual sensing data.

In operation 1230, the processor 1120 may adjust the algorithm based on the real sensing data.

FIG. 13 is a flowchart illustrating operation 1230 in the algorithm adjusting method of FIG. 12.

Referring to FIGS. 12 and 13, when performing operation 1230 of FIG. 12, the processor 1120 may perform operations 1310 through 1380 of FIG. 13.

In operation 1310, the processor 1120 may generate an input vector based on the real sensing data. The description of operation 710 of FIG. 7 may be similarly applied to the generating of the input vector.

In operation 1320, the processor 1120 may extract a feature element from the input vector. The description of operation 720 of FIG. 7 may be similarly applied to the extracting of the feature element.

In operation 1330, the processor 1120 may downsample the input vector. The description of operation 730 of FIG. 7 may be similarly applied to the downsampling of the input vector.

In operation 1340, the processor 1120 may adjust the real sensing data and the virtual sensing data so that the real sensing data and the virtual sensing data may correspond to each other. Because the virtual sensing data is generated through the dynamic simulation, a number of types of the virtual sensing data may be greater than a number of types of the real sensing data, and a format of the virtual sensing data may be different from a format of the real sensing data. Accordingly, the real sensing data and virtual sensing data may be adjusted to correspond to each other.

In operation 1350, the processor 1120 may calculate a probability value of each of preset walking states based on the feature element and the downsampled input vector. The description of operation 740 of FIG. 7 may be similarly applied to the calculating of the probability value.

In operation 1360, the processor 1120 may calculate an error value based on the calculated probability value. In some example embodiments, the processor 1120 may use a supervised learning scheme to calculate the error value, for example, the processor 1120 may perform operation 620 to calculate an error value based on a label and probability value. In other example embodiments, the processor 1120 may use an unsupervised learning scheme to calculate the error value, for example, the processor may perform operation 830 to calculate an error value between virtual sensing data and decoded information.

In operation 1370, the processor 1120 may adjust at least one parameter of the algorithm to reduce the calculated error value. The adjusting of the parameter may be back-propagation. The description of operation 630 of FIG. 6 may be similarly applied to the adjusting of the parameter of the algorithm.

In operation 1380, the processor 1120 may compare the error value with a threshold. A threshold for adjusting of the algorithm may be different from a threshold for training of the algorithm. For example, the threshold for adjusting of the algorithm may be greater than the threshold for training of the algorithm. When the error value is equal to or less than the threshold, the processor 1120 may terminate the adjusting of the algorithm. When the error value exceeds the threshold, the processor 1120 may re-perform operations 1310 through 1370. In other words, the processor 1120 may iteratively perform operation 1230 until the error value is equal to or less than the threshold.

<Use of Algorithm Training Apparatus>

An algorithm training apparatus may be implemented using the above-described method. The algorithm training apparatus may be utilized using various schemes that will be described below. The following description is merely an example, and there is no limitation to the following description.

As discussed in more detail below, in some example embodiments, the controller 140 of the walking assistance apparatus 100 may be configured to perform the operations of one or more of the algorithm training apparatus 300 and the algorithm adjusting apparatus 1100, such that, in some example embodiments, a processor associated with the controller 140 may perform the operations of one or more of the processor 320 and the processor 1120. In other example embodiments, the server 150 may be configured to perform the operations of one or more of the algorithm training apparatus 300 and the algorithm adjusting apparatus 1100, such that, in some example embodiments, a processor associated with the server 150 may perform the operations of one or more of the processor 320 and the processor 1120.

The processor of the controller 140 of the walking assistance apparatus 1 and/or the processor of the server 150 may be programmed with instructions that configure the processor into a special purpose computer to perform the operations illustrated in FIG. 4 and respective sub operations illustrated in one or more of the other figures, discussed above. Therefore, the processor of the controller 140 of the walking assistance apparatus 1 and/or the processor of the server 150 may improve the functioning of the processor itself by producing a large quality of data, for example, virtual sensing data, and using the virtual sensing data to accurately recognize a gait motion.

(1) Server-Client-Based Algorithm Training Apparatus Model (Distribution Model)

The distribution model may be a model in which an algorithm is trained and adjusted by the server 150. The server 150 of the distribution model may include both the algorithm training apparatus 300 and the algorithm adjusting apparatus 1100 such that the processor 320 and the processor 1120 may be a single processor. For example, the server 150 act as the algorithm training apparatus 300 and may generate virtual sensing data and may train an algorithm based on the virtual sensing data by performing operations 410 and 420. Further, the server 150 may act as the algorithm adjusting apparatus 1100 and may receive real sensing data from a client terminal and may adjust the algorithm based on the real sensing data by performing operation 430, and more specifically, by performing operations 910 and 920.

(2) Model in which Algorithm Training Apparatus is Included in Terminal (Integration Model)

The integration model may be a model in which an algorithm is trained and adjusted by a client terminal. For example, the client terminal may be included in the walking assistance apparatus 100, and the processor 320 and the processor 1120 may be a single processor. The client terminal may act as the algorithm training apparatus 300 and may generate virtual sensing data and may train an algorithm based on the virtual sensing data by performing operations 410 and 420. Further, the client terminal may act as the algorithm adjusting apparatus 1100 and may generate real sensing data and may adjust the algorithm based on the real sensing data by performing operation 430, and more specifically, operations 1010 and 1020.

The algorithm training apparatus 300 and the algorithm adjusting apparatus 1100 are provided as individual apparatuses. However, in the integration model, the algorithm training apparatus 300 may include the algorithm adjusting apparatus 1100.

(3) Hybrid Model Obtained by Combining Distribution Model and Integration Model

The hybrid model may be a model in which an algorithm is trained by the server 150 and is adjusted by a client terminal, for example, the walking assistance apparatus 100. In the hybrid model, the server 150 may act as the algorithm training apparatus 300, and the client terminal may act as the algorithm adjusting apparatus 1100, and accordingly the algorithm training apparatus 300 and the algorithm adjusting apparatus 1100 may be understood as individual apparatuses.

For example, the server 150 may act as the algorithm training apparatus 300 and may generate virtual sensing data and may train an algorithm based on the virtual sensing data by performing operations 410 and 420. Further, the client terminal may act as the algorithm adjusting apparatus 1100 and may generate real sensing data and may adjust the algorithm based on the real sensing data by performing operations 1010 and 1020. An initial algorithm may be trained by the server 150 and stored or implemented as data or a chip in the client terminal, for example, in the walking assistance apparatus 100.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method for training an algorithm to recognize a walking state of a user, the method comprising:
    generating virtual sensing data associated with walking of a virtual human model through a dynamic simulation; and
    training the algorithm to recognize the walking state based on the virtual sensing data.

2. The method of claim 1, wherein the generating comprises:
    generating the virtual human model based on a physical characteristic of a virtual human body;
    generating a walking model based on the virtual human model and walking environment information; and
    performing the dynamic simulation based on the walking model to generate the virtual sensing data.

3. The method of claim 2, wherein the generating further comprises:
    associating a virtual sensor to a portion of the virtual human model; and
    generating the virtual sensing data via the virtual sensor.

4. The method of claim 1, wherein the virtual sensing data includes at least one of a joint angle, walking speed data, walking acceleration data, a ground reaction force and an electromyographic (EMG) signal of the virtual human model.

5. The method of claim 1, wherein the algorithm is a deep neural network (DNN).

6. The method of claim 5, wherein the DNN is one of a deep convolutional neural network (DCNN) and a deep belief network (DBN).

7. The method of claim 1, wherein the training comprises:
    calculating a probability value of each of a plurality of walking states using the algorithm based on the virtual sensing data;
    calculating an error value based on the probability value and a label of dynamic simulation data; and
    adjusting at least one parameter of the algorithm to reduce the error value.

8. The method of claim 7, wherein the training further comprises:
    iteratively training the algorithm until the error value is equal to or less than a threshold value.

9. The method of claim 7, wherein the calculating the probability value comprises:
    generating an input vector based on the virtual sensing data;
    extracting a feature element from the input vector;
    downsampling the input vector to generate a downsampled input vector; and
    calculating the probability value based on the feature element and the downsampled input vector.

10. The method of claim 1, wherein the training comprises:
    encoding the virtual sensing data using the algorithm to generate compressed information;
    decoding the compressed information to generate decoded information;
    calculating an error value between the virtual sensing data and the decoded information; and
    adjusting at least one parameter of the algorithm based on the error value.

11. The method of claim 10, wherein the calculating the error value comprises:
    calculating one of a Euclidean distance and a cross entropy between the virtual sensing data and the decoded information.

12. The method of claim 1, further comprising:
    adjusting the algorithm based on real sensing data.

13. The method of claim 12, wherein the adjusting the algorithm comprises:
    receiving the real sensing data from an external terminal;
    adjusting the algorithm based on the real sensing data to generate an adjusted algorithm; and
    transmitting the adjusted algorithm to the external terminal.

14. The method of claim 13, wherein the external terminal is a wearable device.

15. The method of claim 13, wherein the external terminal is a walking assistance apparatus.

16. The method of claim 12, wherein the adjusting the algorithm comprises:
generating real sensing data associated with walking of a person using a sensor; and
adjusting the algorithm based on the real sensing data.

17. The method of claim 16, wherein the real sensing data includes at least one of a joint angle, walking speed data, walking acceleration data, a ground reaction force and an EMG signal of the person.

18. A non-transitory computer-readable storage medium storing a program for causing a processor to perform the method of claim 1.

19. An algorithm training apparatus comprising:
a processor configured to,
generate virtual sensing data associated with walking of a virtual human model through a dynamic simulation, and
train an algorithm to recognize a walking state of a user based on the virtual sensing data; and
a memory configured to store the algorithm.

20. A method of adjusting an algorithm, the method comprising:
acquiring the algorithm, the algorithm trained to recognize a walking state of a user based on virtual sensing data, the virtual sensing data representing walking of a virtual human model through a dynamic simulation;
generating real sensing data associated with a walking of the user using a sensor; and
adjusting the algorithm based on the real sensing data.

21. The method of claim 20, wherein the algorithm is a deep neural network (DNN).

22. The method of claim 21, wherein the DNN is one of a deep convolutional neural network (DCNN) and a deep belief network (DBN).

23. The method of claim 20, wherein the generating the real sensing data comprises:
generating the real sensing data by the sensor of a terminal associated with the user.

24. The method of claim 23, wherein the terminal is a wearable device.

25. The method of claim 23, wherein the terminal is a walking assistance apparatus.

26. The method of claim 20, wherein the real sensing data includes at least one of a joint angle, walking speed data, walking acceleration data, a ground reaction force and an electromyographic (EMG) signal of the user.

27. A non-transitory computer-readable storage medium storing a program for causing a processor to perform the method of claim 20.

28. An algorithm adjusting apparatus comprising:
a memory configured to store an algorithm trained to recognize a walking state of a user based on virtual sensing data, the virtual sensing data representing walking of a virtual human model through a dynamic simulation;
a sensor configured to generate real sensing data associated with a walking of a user; and
a processor configured to adjust the algorithm based on the real sensing data.

29. A controller comprising:
a processor and a memory, the memory containing computer readable code that, when executed by the processor, configures the processor to,
obtain virtual sensing data associated with a virtual user in a dynamic simulation,
train a neural network algorithm to recognize a walking state of a user based on the virtual sensing data,
receive, from one or more sensors real sensing data associated with the user walking in an environment, and
adjust the neural network algorithm based on real sensing data.

30. The controller of claim 29, wherein the virtual sensing data includes at least one of a joint angle, walking speed data, walking acceleration data, a ground reaction force and an electromyographic (EMG) signal of the virtual user.

31. The controller of claim 29, wherein the neural network algorithm is a deep neural network algorithm having a plurality of cascaded processing layers therein connected in such that each successive layer uses an output from a previous layer as an input thereto.

32. The controller of claim 29, wherein the computer readable code, when executed, further configures the processor to train the neural network algorithm by,
calculating an error in the virtual sensing data using one of an unsupervised learning task in which the virtual sensing data is unlabeled and a supervised learning task in which the virtual sensing data is labeled, and
adjusting, via back-propagation, a parameter of the neural network algorithm, to reduce the error below a threshold.

33. The controller of claim 29, wherein the computer readable code, when executed, further configures the processor to recognize the walking state of the user based on the real sensing data and the neural network algorithm trained using virtual sensing data.

34. A walking assistance apparatus comprising:
a driver configured to generate an assistance torque to assist the user with walking;
the one or more sensors configured to sense the real sensing data; and
the controller of claim 33, the controller configured to instruct the driver to generate the assistance torque based on the walking state.

* * * * *